United States Patent [19]

Winter et al.

[11] Patent Number: 4,606,484
[45] Date of Patent: Aug. 19, 1986

[54] TOOL HOLDING APPLIANCE FOR PERSONS WITH LIMITED USE OF HANDS

[75] Inventors: Sybil B. A. Winter, 2773 N. 72nd St., Milwaukee, Wis. 53210; Albert Weiss, Racine, Wis.

[73] Assignee: Sybil B. A. Winter, Milwaukee, Wis.

[21] Appl. No.: 789,192

[22] Filed: Oct. 18, 1985

[51] Int. Cl.$^4$ .............................................. A45F 5/00
[52] U.S. Cl. .................................. 224/218; 224/222; 294/25; 401/8
[58] Field of Search ................. 623/65; 248/291, 349; 211/70; 224/218, 219, 217, 267, 272, 251, 253, 224, 918, 904, 197; 15/443; 401/8, 6, 88; 294/25

[56] References Cited

U.S. PATENT DOCUMENTS

| | | | |
|---|---|---|---|
| 1,094,888 | 4/1914 | Ehrle | 401/8 |
| 1,592,534 | 7/1926 | Mitchel | 224/218 X |
| 2,889,160 | 6/1959 | Nelson | 623/65 X |
| 3,100,363 | 8/1963 | Staver | 401/6 |
| 3,273,766 | 9/1966 | Cosentino | 224/219 X |
| 3,503,546 | 3/1970 | Hunt | 224/218 |
| 3,550,824 | 12/1970 | Bohanski | 224/219 X |
| 3,596,964 | 8/1971 | Zazzara | 224/217 X |
| 3,942,194 | 3/1976 | Winter | 401/8 X |
| 4,148,424 | 4/1979 | Fortenberry | 224/218 |
| 4,165,896 | 8/1979 | Hunt | 294/25 |
| 4,357,717 | 11/1982 | Puhl | 623/65 |

Primary Examiner—Stephen Marcus
Assistant Examiner—Robert Petrik
Attorney, Agent, or Firm—Wheeler Law Firm

[57] ABSTRACT

A tool holding device for persons with limited hand mobility has complementary tool handles and socket of cylindrical or conical form. The socket is integral with a rotatable part and may have an upper open section above the socket diameter permitting tools to be snapped into rotatable relationship with the socket. The rotatable base for the socket is surrounded by an annular fixed housing, and housing and socket base have complementary facing O-ring grooves above which the housing has a locating flange turned inward over the rotatable socket base. The O-ring locates the parts and provides frictional holding force while allowing snap-out snap-in disassembly for cleaning. A strap through the fixed rim retains the parts in assembly and has hook and loop or other easily fastened fasteners for securing the unit to the hand or other limb of the user.

13 Claims, 8 Drawing Figures

TOOL HOLDING APPLIANCE FOR PERSONS WITH LIMITED USE OF HANDS

BACKGROUND OF THE INVENTION

The device of this invention is an improvement of the device of U.S. Pat. No. 3,942,194. The present device is simpler to manufacture and more user friendly, and in some ways is easier to clean and to use. It is lighter in weight and less bulky. It continues to possess the advantages of providing a tool holder that is adaptable to a great variety of tools, and that holds the tools in an infinite variety of positions of rotation around two axes. It thus continues the advantages of the earlier invention and adds new ones.

The other piror art known to applicant is as follows:

| U.S. Pat. No. | Inventor | Dated |
| --- | --- | --- |
| 2,889,160 | Nelson | 6/2/59 |
| 953,821 | Dorrance | 4/5/10 |
| 2,561,523 | Lux | 7/24/51 |
| 2,666,928 | Ameline | 1/26/54 |
| 3,434,163 | Saverino | 3/25/69 |
| 3,490,078 | Perex | 1/20/70 |
| 1,884,739 | Ketcham | 5/5/59 |
| 2,944,846 | Jones | 7/12/60 |
| 3,100,363 | Staver | 8/13/63 |
| 3,358,527 | Lake et al | 12/19/67 |
| 4,357,717 | Puhl | 11/9/82 |

SUMMARY OF THE INVENTION

The invention comprises an improved tool holding device including a rotatable resilient center having an integral socket for a tool which is shaped to be complementary to a special handle on the tool, either in the form of a cylinder or a very slightly tapered cone, the single socket being long enough in the axial direction to give stability to the tool. In the preferred form, the upward side of the socket is open so that the tool may be snapped into place although in an alternate form the cylinder may be closed at the side and the tool inserted end wise as was the case in the earlier patent to Sybil Winter. In either case only a single socket is provided, and each tool for use with the appliance is provided with a handle complementary to the socket and rotatable in the socket to allow positioning of the tool with respect to its own long axis. In addition, the central part of the appliance in which the socket is formed is rotatable about an axis at right angles to the axis of the socket in the outer body of the appliance. A novel mechanism is provided for permitting rotation, but supplying sufficient friction so that unwanted rotation will not occur, permitting disassembly for cleaning, and preventing disassembly at other times. This mechanism includes an outer annular fixed housing having a cylindrical portion which is pierced to receive the attachment strap at two opposite portions of the housing, above which is a groove for an O-ring, and then an inwardly directed flange at the part of the housing most remote from the user's limb.

The inturned flange lies above a portion of the central base of the rotatable body that includes the tool holding socket. Preferably these parts have complementary surfaces such as the surface of a cone and a mating internal cone so that movement of the central tool holder in an outward direction is limited and so that its rotation is guided. The central tool holding part is also provided with an O-ring groove opposite the complementary O-ring groove on the inner portion of the housing. An O-ring is placed in the groove in one of the parts before the two parts are assembled. The O-ring, being readily compressible, can be deformed as the parts are assembled by pushing the central tool holding portion upwardly through the outer housing, and snaps into place to occupy both the O-ring groove in the housing and the O-ring groove in the tool holder. This aligns the parts so that the complementary flange surfaces touch. In that position, the O-ring serves as a friction member to control the rotation of the tool holder with respect to the housing so that moderate force will rotate the tool holder to a new position but so that there is enough friction that it will not move to a new position unless movement is desired. The amount of friction required to cause movement may be varied by changing the specifications of the O-ring or by changing the dimensions of the O-ring channels in one or both of the rim and the tool holder. However, for most applications such changes are unnecessary. When the parts are assembled with the tool holder, the O-ring and the housing in place, the attachment strap may be passed through the opposed slots in the housing. While the strap is in place the housing can not be disassembled from the tool holder. The attachment strap may then be used to secure the device to the limb of a person who requires assistance in holding an implement. Preferably the attachment strap is provided with hook and loop fasteners such as VELCRO at the end so that the attaching strap may be very readily placed about the user's limb. The particular limb may be the hand or arm of the user in the usual case, although there may be some instances in which a person lacking usable arms would place it on the leg. Depending on the needs of the individual, the usual position for the tool holder would be either on the back of the hand of the user, or in the palm of the hand, or across the knuckles of the user.

The tool holding socket is made of a toubh but resilient material having just enough give so that the complementary tool handle may be snapped into place or, if the tool holder is a full cylinder, the tool may be inserted endwise into place. In either case the tool may be placed into the proper rotational position for use and may be rotated by the user to a new position, either by turning it around its own axis or by turning the tool holder around its axis with the housing. Because there is only a frictional engagement rather than stops, the tool may be placed in any rotational position and at any angle with respect to the limb, and the present device is much less cumbersome on the limb of the patient than previously known devices. The latter is an extremely important advantage. In addition, the device is readily manufactured. It may readily be disassembled for cleaning simply by removing the strap from the opposed slots and pressing downwardly on the tool holder to snap the tool holder free of the O-ring and the housing. If the O-ring becomes worn, it is easy to replace since O-rings are a standard commodity. O-rings and plastic parts are easily cleaned. Sanitation is an important consideration in appliances for the handicapped or those with limited mobility.

DRAWINGS

Figures 5, 6, 7:
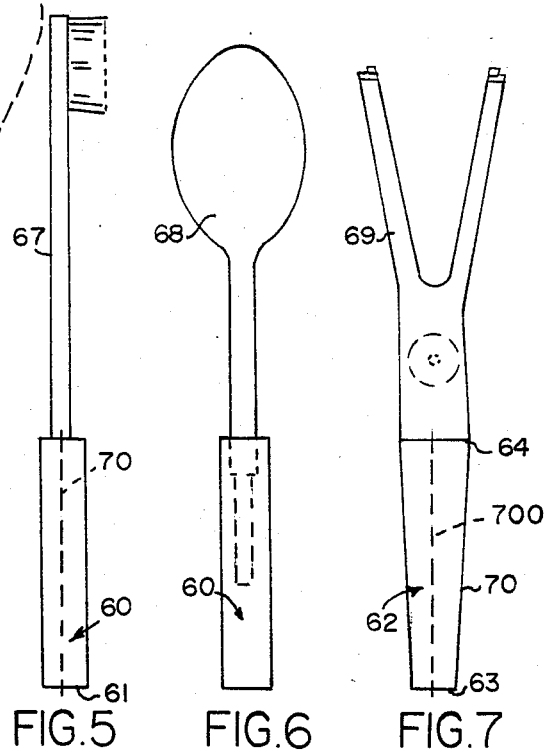

FIGS. 5, 6, and 7 are three of the tools having handles shaped to fit within the socket of our device. The handles in FIG. 5 and FIG. 6 are cylindrical to fit the sockets shown in FIGS. 4 and 8 while the handle of FIG. 7 is slightly cone-shaped to fit in the complementary socket of FIG. 8.

Figure 8:
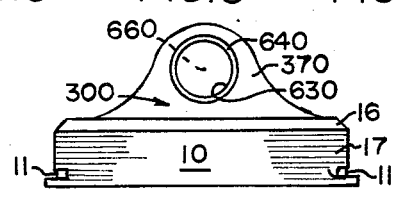

FIG. 8 is a side view of a modified form our our device in which the tool socket rather than being open at the top is a full circle about the axis and in which the socket is slightly cone-shaped to take tools having the handle of the form shown in FIG. 7 rather than the form in shown in FIGS. 5 and 6.

DETAILED DESCRIPTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto. p The basic form of the invention is that shown in FIGS. 1 through 6. In those views, the tool socket is a true cylinder having an axis generally at right angels to the coaxial axes of the fixed body and the rotatable body and open at the top, that is at one side of the cylinder, but substantially above the axis of the cylinder.

The form of the device shown in FIGS. 7 and 8 has two variations which may be used together or separately. One variation is that the socket is not open at the top but is a complete circle so that the tool must be inserted from the end rather than from the top. The other variation is that as shown the socket is sligthly cone-shaped rather than a true cylinder to receive the handle of FIG. 7 which is a complementary cone. It should be noted that the cylinder of FIG. 1 may be cone-shaped without being closed on top, and the closed socket of FIG. 8 may be truly cylindrical. For convenience of views, both modifications have been shown together in a single modified form in FIG. 8. Likewise, all the tools of FIGS. 5 through 7, and other tools not shown, may have either a cylindrical handle if the socket is cylindrical or it may have the conical form required for the conical socket shown in FIG. 8. Either socket may have an open top as in the socket of FIG. 1 or may be closed like the socket of FIG. 8.

Figure 1:
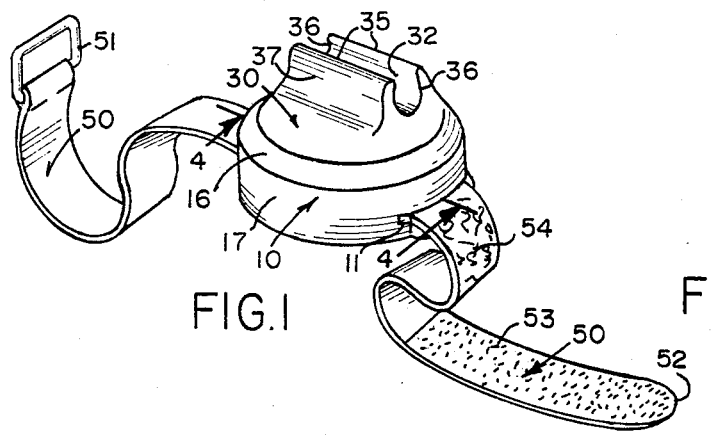
FIG. 1 is a perspective view of the improved tool holding appliance for persons with limited use of hands of our invention.

As best illustrated in FIG. 1, our device has a fixed body 10, consisting mainly of a rim 17 around a rotatable body 30, and a strap 50, with which are associated a variety of tools such as toothbrush 67, spoon 68 and floss holder 69, each having handles 60 or 62 to fit the socket on the rotatable body. The tools themselves that are illustrated in FIGS. 5, 6, and 7 are merely illustrative of the many kinds of tools that might be used with our device. The important thing is that they have a handle 60 or 62 to fit the socket.

Looking at FIG. 1, strap 50 is generally conventional. It has a ring 51 through which strap end 52 may be passed and doubled back so that the two sections 53 and 54 of the hook and loop material may engage one another and secure the strap. Other forms of strap may be used but that form is particularly convenient for persons having limited ability to fasten a strap and it is accordingly very appropriate for a device for use by persons having limited mobility. The strap 50 passes through a pair of slots 11 provided at opposite sides of fixed body 10. The slots are best seen in the crosssectional view of FIG. 4 and the side view of FIG. 8.

Figure 3:
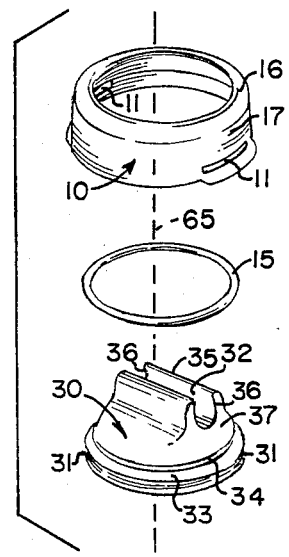
FIG. 3 is an exploded view of our device with the wrist strap removed and with the parts separated along the axis of rotation of the rotatable body within the fixed body, the axes of the two bodies being coaxial.
Figure 4:
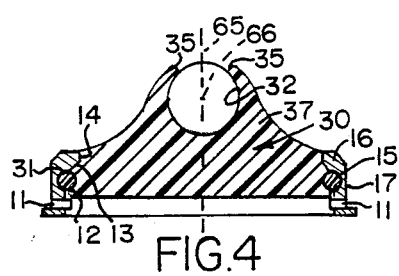
FIG. 4 is a cross-sectional view on lines 4—4 of FIG. 1 with the rotatable body turned so that the axis of the tool in the tool socket is in line with the point of view.

As best seen in FIGS. 3 and 4, rotatable body 30 does not fill circumferential rim 17 of fixed body 10 but extends only to the level of slots 11 so that when the strap 50 is in place through slots 11, it lies underneath rotatable body 30 and prevents it from being withdrawn from fixed body 10. However, it is extremely easy to pull the strap 50 out of slots 11 so that the entire device may be disassembled for cleaning.

Fixed body 10 is provided on its interior surface, with a groove 12. Rotatable body 30 is provided with an opposed groove 31. O-ring 15 is received in the space between groove 31 and groove 12 when the device is assembled along the coaxial axes 65 (FIG. 4) of fixed body 10 and rotatable body 30 (as shown in FIG. 3) to the position shown in FIG. 4. Becuase the O-ring 15 is resilient, and because there is a small difference in the outer diameter of the rotatable body 30 compared with the inner diameter of fixed body 10, the parts can be placed in the position shown in FIG. 3 and rim 17 fixed body 10 may be pushed down over rotatable body 30, or vice versa, to snap the parts together until flange 16 engages it in the correct position. The strap 50 is then installed through slots 11 to keep the parts assembled.

Figure 2:
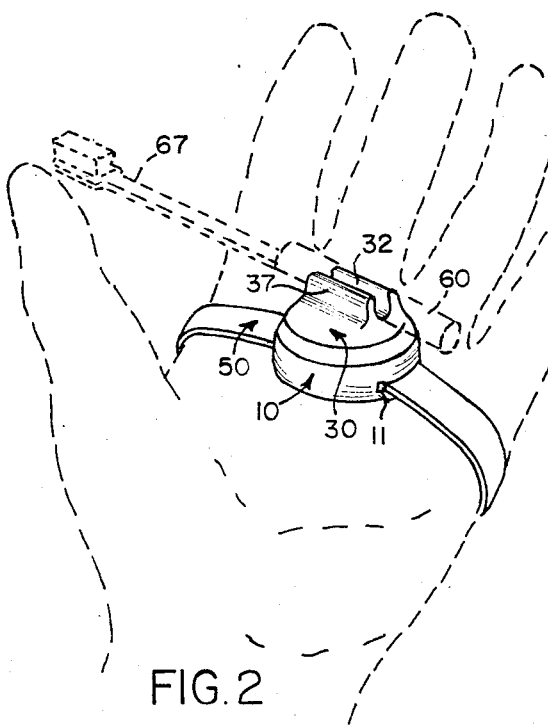
FIG. 2 is a perspective view of our device as it would appear mounted on a human hand which is shown in broken lines and having the tool of FIG. 5 which also shown in broken lines in place for use.

In addition to its function to keep the parts assembled, O-ring 15 acts as a friciition member between fixed body 10 and rotatable body 30. It is so sized with respect to grooves 12 and 31 that it frictionally resists turning of rotatable body 30 about the mutual axis 65 of fixed body 10 (FIG. 4) and rotatable body 30 while permitting such movement if a reasonable amount of force is applied. A person whose hand mobility is not too limited can simply turn rotatable body by grasping the socket portion 37 by hand and placing it in the desired roratative position. A person with more limited mobility may place a tool such as those of FIGS. 5, 6 or 7 in the scoket 32 as shown in FIG. 2 and may then exert leverage against the end of the tool to place rotatable body 30 in the appropriate position for us of the tool. However the resistance caused by the presence of O-ring 15 in grooves 12 and 31 is sufficient that with reasonable care the tool will not move to an unwanted position during use. Thus this extemely simple mechanism accomplishes a number of purposes.

Rotatable body 30 is provided with two surfaces to guide its rotation. Surface 33 is cone-shaped as best seen in FIG. 4 and surface 34 is a circumferential vertical abutment. Both surfaces are coaxial with the axis 65 of rotatable body 30. Fixed body 10 is provided with corresponding surfaces. Cone-shaped surface 13 coaxial with axis 65 ridges against surface 33 of rotatable body 30 and a circular vertical abutment 14 coaxial with axis 65 engages the similar surface 34 complementary to it on rotatable body 30. The surfaces are held in the proper relationship by O-ring 15.

Socket 32 is cylindrical in form in FIG. 1 but is open at the top to form a pair of lips 35 in the form shown in FIGS. 1 through 4. Socket 32 has an axis 66 at right angles to axis 65 and above fixed body 10. Complementary tool handle 60 may be placed in socket 32 by snapping it between lips 35 or inserting it endwise at either end 36 of socket 32. Socket protion 37 of rotatable body 30 is preferably gently curved and rises only a little above fixed body 10.

It should be noted that if the tool handle 62 is slightly conical having a smaller end 63 and a larger end 64 (FIG. 7), the socket 32 must also be conical as is shown in FIG. 8, even though the top may be open as shown at lips 35 in FIG. 1, and end 63 of handles 62 must be inserted first into the larger end of the socket 32 if it is inserted endwise. However it will still be true that the handle may be placed endwise into socket 32 along axis 66 or may be snapped into the socket between lips 35. It will be understood that whichever form is adopted for socket 32, all of the handles will be of the form 60 if the socket 32 is cylindrical or of the form 62 if the form of the socket 32 is conical.

Desirably the material of rotatable body 30 and socket 32 is such that it is hard and is easy to clean,, tough but slightly resilient, and with a sufficient coeffecient of friction with respect to the handles 60 or 62 of the tools as to offer resistance to turning of the tools about axis 66 so that when the tools are placed in an approprite orientation by the user, they will tend to remain in that orientation despite the stress of use. Devices that have been built of various types of plastic display the necessary characeristics. There is believed to be a wide range of plastic materials that would be suitable. Similar considerations apply to the material of the fixed body, and the handles 60 or 62. In each case the parts must be durable, easy to clean, and offer sufficient coefficient of friction when placed in operating position so that the tools will remain in place.

It should be noted that the hand shown in FIG. 2 is shown very sketchily and in phantom because it may represent either the back of the hand or the front of the hand and may represent either hand. Although the device is shown mounted on a hand, it may also be mounted across the knuckles of the hand or if the individual lacks effective hands, it may be mounted on an arm. If the person lacks effective arms and has sufficient leg mobility, it is even possible to mount the device of our invention on a leg.

It should also be noted that although FIGS. 5, 6 and 7 show respectively a tooth brush, a spoon, and a dental floss holder as the tools to be used with our device, these are merely illustrative of an unlimited range of tools that may be provided with handles 60 or 62. It is the presence of the handle 60 or 62 that is important for our invention and not the nature of the tool to which the handle is attached, which can include any tool that the person wishes to use.

When it is desired to change tools, it is necessary only to apply sidewise pressure in the direction of lips 35 on a tool having a handle 60 or 62 to snap the tool out of socket 32, or to aply endwise pressure on end 61 or small end 63 to push the tool along axis 66 to remove it from socket 32 or 320 so that the tool may be cleaned, stored, or replaced by another tool. In many instances, even a person of limited mobility may readily replace one tool with another. Even if the tool must be replaced by a helper, many persons of limited mobility will be able to use tools with the help of using this device who could not do so using other aids. Furthermore, the way that the socket is formed and the way that the tool fits into the socket tend to produce a socket with a long life and a good fit for the tool over a long life so that the device for our invention will be relatively trouble free.

Looking now at the modification shown in FIG. 8, it will be observed that the fixed body 10 is the same as it would be in the modification of FIGS. 1 through 4. Likewise the tools such as those illustrated in FIGS. 5, 6 and 7 may be used with handles 62 in socket 320 shown in FIG. 8. The handle must be of the form 52 shown in FIG. 7 becuase conical socket 320 has a large end 321 and a small end 322 so that when small end 63 of handle 62 is inserted first into large end 321 it is held firmly with axis 700 coincident with axis 660 of socket 320, just as in socket 32 handle 60 is held firmly with axis 70 coincident with axis 66. Socket portion 370 may be turned on axis 65 of fixed body 10 to position handle 62 and the attached tool such as 67, 68, 69.

Changing utensils can sometimes be accomplished by the user. No finger coordination and very little wrist motion is necessary.

To pick up a utensil, position one end of the snap-action clip over the circular grip. Now by pushing down and rotataing the arm or wrist, the utensil will snap into the clip.

To eject the utensil, place the end of the circular grip (or the opposite end of the utensil) against the table top and push down releasing the utensil from the snap-action clip.

In the event that it is desired to mount a tool in the device that may be turned with some force, such as a key or a screwdriver, it may be desirable to prevent the turning of the tool by providing the handle 60 with an axially extending ridge which fills the space between lips 35 of the socket so that only a single orientation of the handle 60 is possible. Such an abutment could have parallel walls, or the walls could incline outwardly at an outward angle to a radial line to better capture the lips 35 and prevent rotation of handle 60.

We claim:

1. In a tool holding appliance, a tool holding socket, a rotatable body that is a tool holding socket support, and a fixed body having an axis on which said rotatable body is rotatable, said fixed body being provided with slots to receive an attachment strap for attaching said body to the limb of a user, the novelty comprising:

the fixed body comprising a circumferential outer rim about the rotatable body having an axis coaxial with the axis of the fixed body, the rotatable body being provided with an outwardly opening circumferential O-ring groove and said fixed body being provided with an inwardly opening O-ring groove complementary to said outwardly opening O-ring groove whereby an O-ring may be placed in one of said grooves and the rotatable body and the rim may be snapped together with the O-ring snapping into said complementary grooves to retain the parts assembled, the O-ring being of a size to control the frictional engagement between the parts by engagement with said grooves whereby to hold the rotatable body in a desired position unless a force greater than the frictional force between the O-ring and the grooves is exerted by a user.

2. The device of claim 1 in which the rotatable body member is provided with an integral tool holding socket spaced upwardly from said rim enough so that a tool may be placed in said socket above the rim, the socket being a single circular opening having an axis located above and substantially parallel to the diameter of the rotatable body, said rotatable body and socket being constructed of a material that is hard and smooth and which provides sufficient friction with the handle of a tool placed in said socket so that the complementary surfaces of the tool handle and the socket retain the tool in an adjusted position without the need of other clamping means.

3. The device of claim 2 in which the complementary socket and tool handle are each substantially cylindrical.

4. The device of claim 2 in which the complementary socket and tool handle are each slightly tapered cones.

5. The device of claim 3 in which the socket is a complete circle.

6. The device of claim 4 in which the socket is a complete circle.

7. The device of claim 3 in which the socket is open at the top at a level higher than the axis.

8. The device of claim 4 in which the socket is open at the top at a level higher than the axis.

9. The device of claim 2 in which the socket is open upwardly at one side above the horizontal plane at the diameter of the socket to form lips between which a tool may be snapped into place in the socket from the upwardly facing side of the socket.

10. The device of claim 2 in which the socket and the rotatable body are integrally formed of a single body of plastic.

11. The device of claim 1 in which the rim of the fixed body has an inwardly turned flange extending over the edge of rotatable body.

12. The device of claim 11 in which the upper surface of the rotatable body and the lower surface of the inward flange of the rim of the fixed body are provided with complementary surfaces that bear against one another when the parts are assembled to guide rotation of the socket member with respect to the rim member.

13. The device of claim 12, said complementary surfaces including conical portions.

* * * * *